(12) United States Patent
Burns, Jr. et al.

(10) Patent No.: US 6,926,701 B2
(45) Date of Patent: Aug. 9, 2005

(54) DISPOSABLE EXCRETA MANAGEMENT DEVICE

(75) Inventors: John Glasgow Burns, Jr., Kobe Hyogo (JP); Maya Hasegawa, Ashiya Hyogo (JP); Takaya Okano, Kobe Hyogo (JP); Yoko Hayashi, Osaka (JP)

(73) Assignee: The Proctor & Gamble Company, Cincinnati, OH (US)

( * ) Notice: Subject to any disclaimer, the term of this patent is extended or adjusted under 35 U.S.C. 154(b) by 125 days.

(21) Appl. No.: 10/459,185

(22) Filed: Jun. 11, 2003

(65) Prior Publication Data

US 2004/0002687 A1 Jan. 1, 2004

Related U.S. Application Data

(60) Provisional application No. 60/392,894, filed on Jul. 1, 2002.

(51) Int. Cl.7 ............................. A61F 5/44; A61M 31/00
(52) U.S. Cl. ........................................ 604/344; 604/277
(58) Field of Search ................................ 604/277, 327, 604/332–345, 355

(56) References Cited

U.S. PATENT DOCUMENTS

| | | | | |
|---|---|---|---|---|
| 3,577,989 A | | 5/1971 | Anderson | |
| 4,211,224 A | * | 7/1980 | Kubach et al. | 604/333 |
| 4,490,145 A | * | 12/1984 | Campbell | 604/333 |
| 4,911,699 A | * | 3/1990 | Fenton | 604/333 |
| 4,938,750 A | * | 7/1990 | Leise, Jr. | 604/333 |
| 5,976,118 A | * | 11/1999 | Steer | 604/332 |
| 6,015,399 A | * | 1/2000 | Mracna et al. | 604/332 |
| 6,050,983 A | * | 4/2000 | Moore et al. | 604/333 |
| 6,066,120 A | * | 5/2000 | Whiteside | 604/332 |
| 6,129,716 A | * | 10/2000 | Steer | 604/333 |
| 6,135,986 A | * | 10/2000 | Leisner et al. | 604/322 |
| 6,165,159 A | * | 12/2000 | Blanton | 604/333 |
| 6,171,288 B1 | * | 1/2001 | Wiltshire | 604/333 |
| 6,231,553 B1 | * | 5/2001 | Hulett | 604/333 |
| 6,350,256 B1 | * | 2/2002 | Palumbo et al. | 604/339 |
| 6,464,674 B1 | * | 10/2002 | Palumbo et al. | 604/385.01 |
| 6,506,184 B1 | * | 1/2003 | Villefrance | 604/333 |
| 6,685,685 B2 | * | 2/2004 | Sugita et al. | 604/355 |
| 6,726,667 B2 | * | 4/2004 | Leise et al. | 604/339 |
| 2002/0010444 A1 | * | 1/2002 | Wiltshire et al. | 604/335 |
| 2002/0193762 A1 | * | 12/2002 | Suydam | 604/327 |
| 2003/0187393 A1 | * | 10/2003 | Cline | 604/131 |
| 2003/0204173 A1 | * | 10/2003 | Burns et al. | 604/337 |

FOREIGN PATENT DOCUMENTS

JP        07124189 A        5/1995

* cited by examiner

*Primary Examiner*—Larry I Schwartz
*Assistant Examiner*—Michael G. Bogart
(74) *Attorney, Agent, or Firm*—Kevin C. Johnson; Michael S. Kolodesh

(57) ABSTRACT

The disposable excreta management device has a longitudinal centerline, a transverse centerline, a wearer-facing surface and an opposing surface. The disposable excreta management device comprises a flexible bag to contain excreta and an adhesive flange to attach the device to the body of a wearer. The flexible bag has an opening positioned on the wearer-facing surface. The excreta management device has an orifice provided on the flexible bag and comprises a seal means to resealably close the orifice. A peel force of the seal means to the surface of the flexible bag is between 0.3 N/cm and 4.0 N/cm.

6 Claims, 9 Drawing Sheets

DISPOSABLE EXCRETA MANAGEMENT DEVICE

CROSS REFERENCE TO RELATED APPLICATION

This application claims the benefit of U.S. Provisional Application No. 60/392,894, filed on Jul. 1, 2002.

FIELD OF THE INVENTION

The present invention relates to an excreta management device used for babies, children or adults. More particularly, the present invention relates to an excreta management device comprising an adhesive flange and a flexible bag having an orifice for insertion of instruments or solid medicines such as wipes, an enema syringe, a suppository, and the like.

BACKGROUND

Excreta management devices are known as articles that are designed to be worn principally by incontinence sufferers and in particular by bedridden patients. Such excreta management devices are attached to the perianal area or urethral area of a wearer and are intended to entrap and immediately contain fecal material, urine and other bodily discharges.

A representative excreta management device is disclosed in, e.g. U.S. Pat. No. 3,577,989. It discloses a disposable elimination-trapping bag comprising a sack having an open-top portion and a thin annular oval-shaped flange secured to the sack around the open-top portion. The flange comprises a layer of adhesive material as a means of attaching the disposable bag to a wearer. The disposable bag is specifically designed for attachment to a wearer in the vicinity of the anus.

Such an excreta management device is adhesively attached to the wearer's skin around an excretory orifice, such as an anal orifice, a urethra orifice or the like during the use of the device. When the excreta management device is used for incontinence sufferers or bedridden patients who cannot control defecation, caregivers need to frequently remove the devise from the wearer's skin in order to give a treatment, such as an enema, insertion of a suppository or the like to facilitate regular defecation. However, frequent removal of the device from the wearer's skin may damage the wearer's skin since the device is firmly attached to the wearer's skin to prevent leakage of discharged excreta. Particularly, it may lead to a serious skin problem for wearers having sensitive skin.

Japanese Patent Laid-Open publication No. 124189/1995 published on May 16, 1995, discloses another excreta management device comprising a bag for containing discharged fecal material. The bag is provided with an opening, an adhesive part surrounding the opening and a release paper covering the adhesive part. The device further has a discharge part to discard the fecal material stored in the bag. The user discards the fecal material by tearing the discharge part open along the perforations or by opening the zipper. However, in the case of perforations, once the user tears the discharge part open along the perforations, it is impossible to close the discharge part again. In the case of a zipper, the seal means of the zipper is not generally strong enough to prevent the zipper from opening by pressure exerted by movement of the wearer. Therefore, the discharge part must be pressed by the wearer's body (e.g., buttocks) during the use of the device such that the zipper of the discharge part does not open.

Accordingly, there still exists a need for an excreta management device which allows caregivers to easily make treatment, such as an enema, insertion of a suppository without removing the device from the wearer's skin. Additionally, there also exists a need for an excreta management device having an orifice for such a treatment, and a seal means to resealably close the orifice while the device is worn so as to prevent leakage of discharged excreta through the orifice by pressure exerted by movement of the wearer (or the discharged excreta itself).

SUMMARY

The disposable excreta management device has a longitudinal centerline, a transverse centerline, a wearer-facing surface and an opposing surface. The disposable excreta management device comprises a flexible bag to contain excreta and an adhesive flange to attach the device to the body of a wearer. The flexible bag has an opening positioned on the wearer-facing surface. The excreta management device has an orifice provided on the flexible bag and comprises a seal means to resealably close the orifice. A peel force of the seal means to the surface of the flexible bag is between 0.3 N/cm and 4.0 N/cm.

BRIEF DESCRIPTION OF THE DRAWINGS

While the Specification concludes with claims which particularly point out and distinctly claim the invention, it is believed the present invention will be better understood from the following description of preferred embodiments taken in conjunction with the accompanying drawings, in which like reference numerals identify identical elements and wherein:

DETAILED DESCRIPTION

Figure 1:
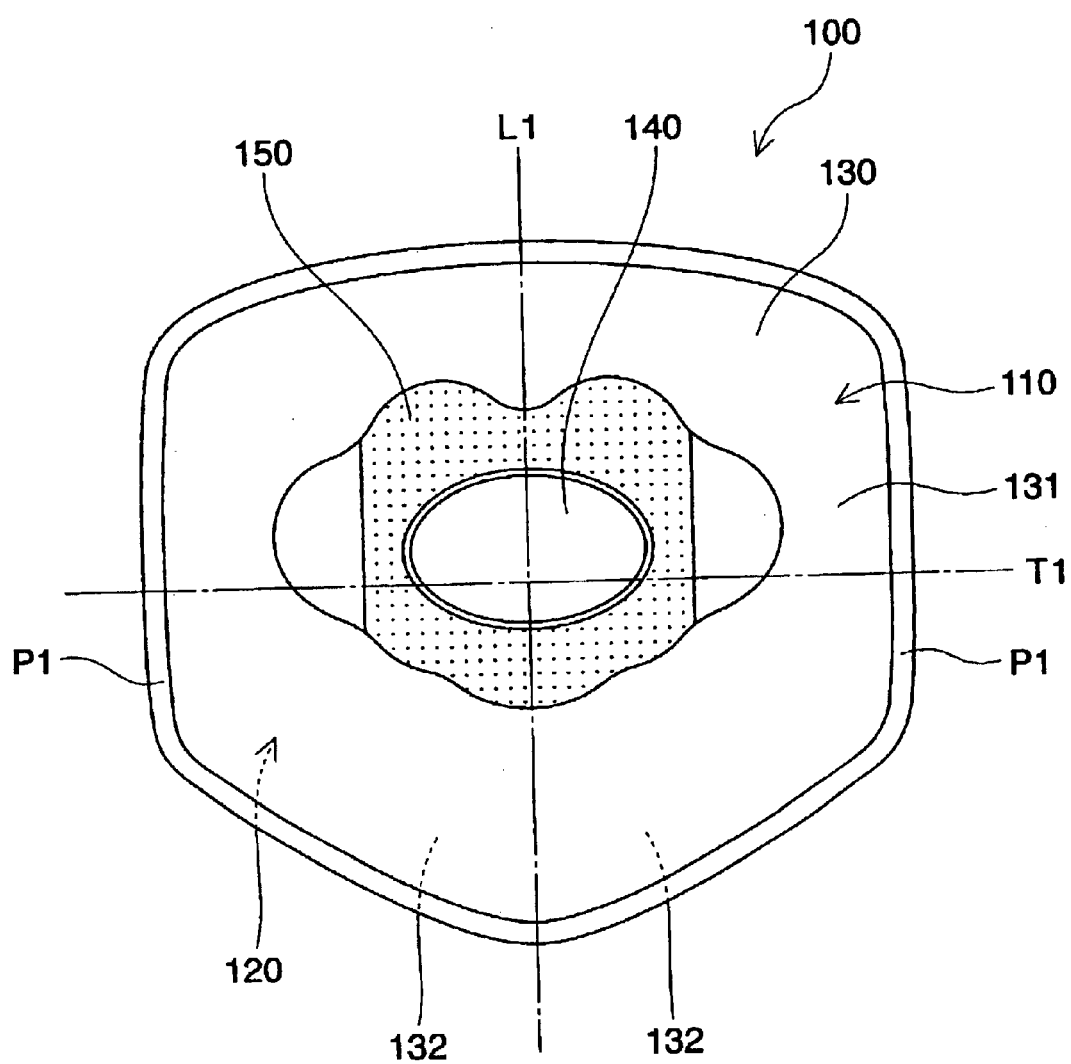
FIG. 1 is a top plan view of one embodiment of an excreta management device of the present invention.

All cited references are incorporated herein by reference in their entireties. Citation of any reference is not an admission regarding any determination as to its availability as prior art to the claimed invention.

The definitions of several terms are first provided to assist the reader in understanding the present invention.

The term "comprising", as used herein, means that other steps and other ingredients which do not affect the end result can be added. This term encompasses the term "consisting of" and "consisting essentially of".

The term "disposable", as used herein, describes devices which generally are not intended to be laundered or otherwise restored or reused (i.e., they are intended to be discarded after a single use and, preferably, to be recycled, composted or otherwise disposed of in an environmentally compatible manner.)

The term "excreta" or "bodily discharges", as used herein, are interchangeable, and includes all discharges released from an excretory orifice of a human body, including fecal materials, urine, menses, and the like.

The term "excretory orifice", as used herein, refers to an orifice which excreta pass through to discharge the excreta from the human body when excretion occurs. Such an excretory orifice includes urethra, vaginal orifice, anus, and the like.

FIGS. 1 to 4 show one embodiment of a disposable excreta management device of the present invention which is disposed to the skin around the excretory orifice (e.g., a perianal area) of a wearer. The excreta management device 100 shown in FIGS. 1 and 4 has a longitudinal centerline L1. The term "longitudinal", as used herein, refers to a line, axis or direction in the plane of the device 100 that is generally aligned with (e.g., approximately parallel to) a vertical plane which bisects a standing wearer into left and right body halves when the disposable excreta management device 100 is worn. The excreta management device 100 shown in FIGS. 1 to 4 also has a transverse centerline T1. The terms "transverse" or "lateral", as used herein, are interchangeable, and refer to a line, axis or direction which lies within the plane of the disposable excreta management device 100 that is generally perpendicular to the longitudinal direction. The excreta management device 100 shown in FIGS. 1 to 4 has two surfaces; one is a wearer-facing surface 110 and the other is an opposing surface 120. The wearer-facing surface 110 is the surface of the device 100 which is generally oriented toward the wearer when the device 100 is worn. The wearer-facing surface 110 typically at least partially comes in contact with the wearer's skin during the use of the device 100. The opposing surface 120 is the surface of the device 100 which is generally oriented away from the wearer when the device 100 is worn, and at least partially toward a garment if a garment is worn. In a preferred embodiment, the opposing surface 120 of the device 100 may be at least partially, more preferably wholly, transparent or translucent.

The excreta management device 100 comprises a flexible bag 130 having an opening 140, an adhesive flange 150 surrounding the opening 140, an assistant tab 160 disposed on the opposing surface 120 of the device 100. The excreta management device 100 has an orifice 170 provided on the flexible bag 130 and comprises a seal means to resealably close the orifice 170. In a preferred embodiment shown in FIGS. 1 to 4, the seal means may comprise an orifice cover 180 attached to the flexible bag 130 to cover the orifice 170. Alternatively, the seal means may comprise a zip fastener provided around the orifice 170. The term "orifice", as used herein, refers to a narrow or wide opening provided to an object. Such an orifice includes a hole, an aperture, a cut, a slit, a gap, a crack, a notch, a channel, a trench, and the like. The term "resealable" or "resealably", as used herein, means that an orifice is closed by an orifice cover again not to cause leakage of discharged excreta through the orifice after the orifice is exposed by removing the orifice cover.

The flexible bag 130, as used herein, is a flexible receptacle for the containment of discharged excreta, such as fecal materials, urine or the like. The bag 130 can be provided in any shape or size depending on the intended use thereof, i.e., whether the device is intended for bedridden patients or active patients suffering from incontinence. For example, elongated bags which are principally tubular or rectangular may be typically utilized by bedridden patients and elderly incontinence sufferers. For more active wearers such as infants or adults, the flexible bag 130 should preferably be anatomically shaped such that the excreta management device 100 comprising the bag 130 follows the contours of the body and can be worn inconspicuously by the wearer under normal garments. Particularly, preferred shapes are three-dimensional shaped bags such as cubic shaped bags, spherical shaped bags, conical (or truncated conical) shaped bags, pyramidal (or truncated pyramidal) shaped bags, tetrahedral (or truncated tetrahedral) shaped bags, cylindrical shaped bags or the like. Further, when the bag is not expanded, the bag may have a substantial circular, oval, square, rectangular, polygonal shape. In a preferred embodiment shown in FIGS. 1 to 4, the bag 130 is a substantial polygonal shape having 5 sides, which is transversely asymmetric, when the bag 130 is not expanded.

The bag 130 is preferably designed to provide sufficient volume for excreta under a variety of wearing conditions, e.g., when the device 100 is worn by active wearers (i.e., not bedridden wearers). The bag 130 is designed to safely contain any entrapped material, typically it will be liquid impermeable, yet it may be breathable. The bag 130 is designed to having sufficient strength in order to resist rupturing in use, e.g., when pressure on the bag 130 is exerted in typical wearing condition such as sitting.

The bag 130 may be made from a unitary piece of material or from a number of separate pieces of material, which may be identical or different and which are sealed at their respective peripheries, depending on the shape of the bag 130 required. In the embodiment shown in FIGS. 1 to 4, the flexible bag 130 is made from two separate sheets. The bag 130 is made from a wearer-facing sheet 131 and an opposing sheet 132. In the embodiment shown in FIGS. 1 to 4, the wearer-facing sheet 131 and the opposing sheet 132 substantially form the wearer-facing surface 110 and the opposing surface 120 respectively. The wearer-facing sheet 131 and the opposing sheet 132 are sealed along the periphery P1 of the sheets 131 and 132 by means known to the person skilled in the art, such as heat seal, adhesive, or the like, in order to form the bag 130. In a preferred embodiment, the opposing sheet 132 may be at least partially, more preferably wholly, transparent or translucent such that caregivers can easily observe condition of discharged excreta such as fecal material through the opposing sheet 132 in order to monitor the wearer's health condition. In addition, such a partially/wholly transparent/translucent opposing sheet 132 helps caregivers attach the device 100 to the skin around the wearer's excretory orifice (e.g., the anus) since the caregivers can easily recognize the position of the wearer's excretory orifice through the opposing sheet 132.

Figure 2:
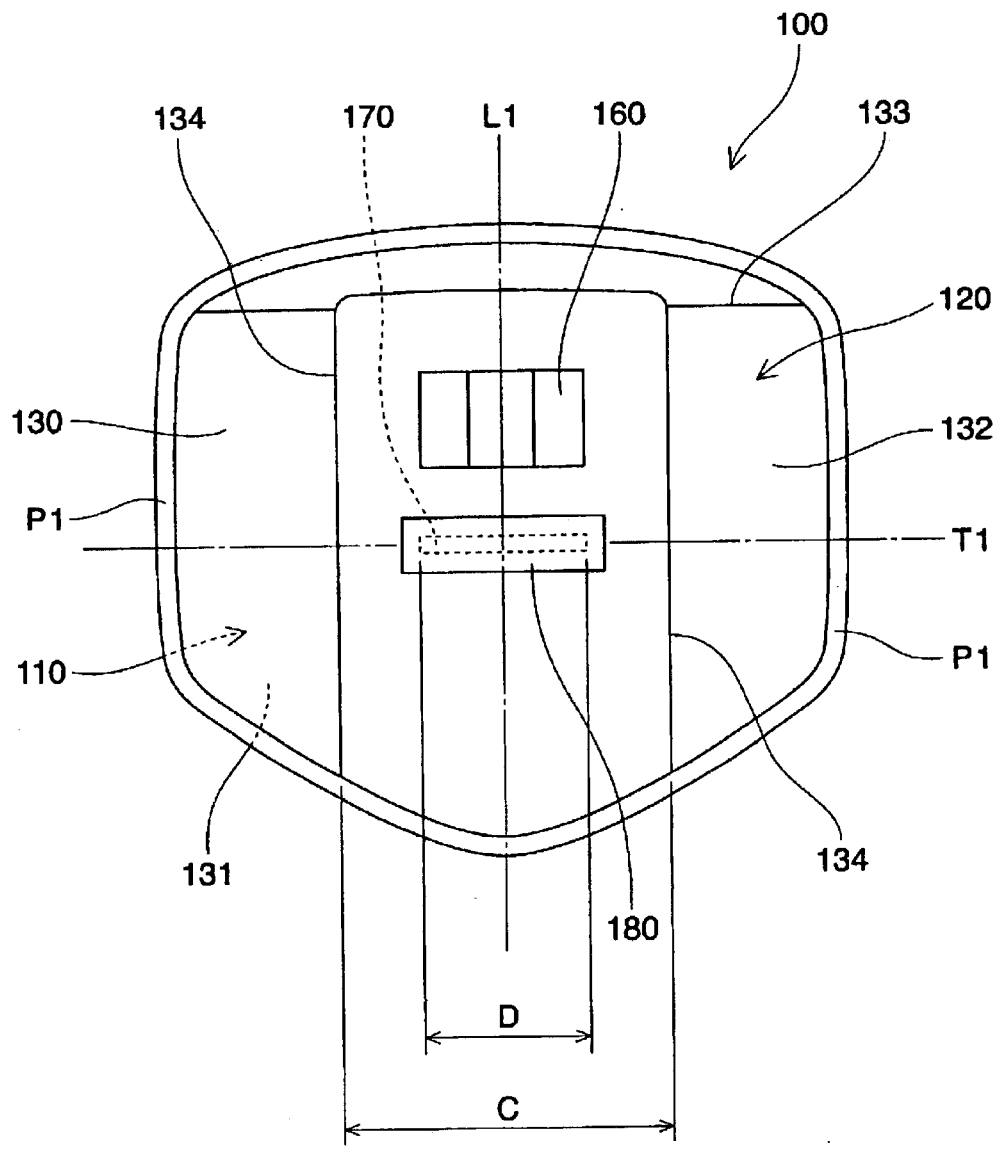
FIG. 2 is a bottom plan view of the excreta management device of FIG. 1.
Figure 4:
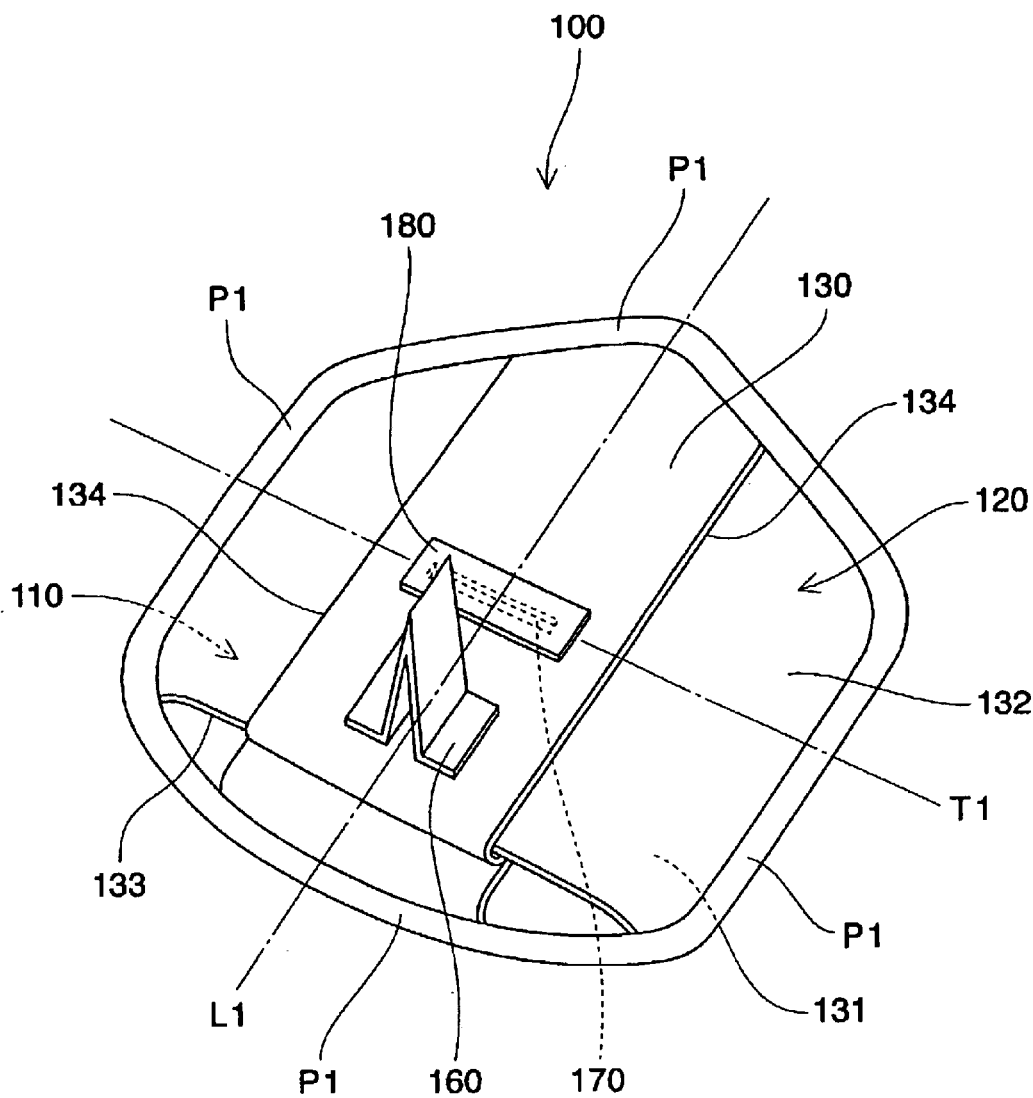
FIG. 4 is a perspective view showing the opposing surface of the excreta management device of FIG. 1.

The bag 130 preferably has at least one fold provided on the opposing surface 120 in order to allow the bag 130 to expand vertically when the bag 130 contains excreta. The number of the fold will obviously depend upon the circumstances, e.g., a configuration of the bag, a size of the bag and/or a material of the bag. In the embodiment shown in FIGS. 2 and 4, the folds 133 and 134 are formed on the opposing surface 120 of the device 100 such that the bag 130 can expand vertically to have a three-dimensional shape when defecation occurs. The expansion of the bag 130 provides extra storage capacity in use. The fold 133 has an alphabet "Z"-like configuration in the cross-sectional view of the opposing surface 120 of the device 100 taken along the longitudinal centerline L1. Thus, such a fold is referred to as "Z-fold" herein. In the embodiment shown in FIGS. 2 and 4, one Z-fold oriented in the transverse direction is formed on the opposing surface 120 of the device 100. The other folds 134 oriented in the longitudinal direction are formed on the opposing surface 120 of the device 100 as shown in FIGS. 2 and 4. The folds 134 comprise two Z-folds oriented in the longitudinal direction. The two Z-folds 134 are disposed oppositely with respect to the longitudinal centerline L1 and parallel to the longitudinal centerline L1. The combination of the two opposite Z-folds has a Greek letter "Ω (OMEGA)" like configuration in the cross-sectional view of the opposing surface 120 of the device 100 taken along the transverse centerline T1. Such a combination of two opposite Z-folds is referred to as "OMEGA-fold" herein. Thus, one Z-fold 133 and one OMEGA-fold 134 are formed on the opposing surface 120 of the device 100 in the embodiment shown in FIGS. 2 and 4.

The bag 130 can comprise one or multiple layers, preferably two or three layers. The layer positioned on the inside of the bag, which will typically at least partially come in contact with excreta, is called the inner layer. The outermost layer of the bag 130, which will typically at least partially come in contact with the skin of a wearer and the garments of the wearer, is called the outer layer. The layer of the bag 130 may be provided from any material such that the bag 130 is liquid impervious. The layer may in particular comprise any material such as a nonwoven or a polymeric film. In a preferred embodiment, the layer may be formed from a laminate comprising a nonwoven layer and a polymeric film. In one preferred embodiment, the bag 130 comprises two layers, which comprises a nonwoven layer and a film. Alternatively, the bag 130 may comprise three layers; one film layer and two nonwoven layers, or two film layers and one nonwoven layer.

Suitable nonwoven layers for the bag 130 may comprise felt fabrics, spunlaced fabrics, fluid jet entangled fabrics, air-laid fabrics, wet-laid fabrics, dry-laid fabrics, meltblown fabrics, staple fiber carding fabrics, spunbonded fabrics, stitch-bonded fabrics, apertured fabrics, combinations of the above or the like. The nonwoven layer or the nonwoven layers constituting the bag 130 may be hydrophobic or hydrophilic. For example, if the bag 130 comprises a film layer, the nonwoven layers may be hydrophilic or hydrophobic. If the bag 130 does not comprise a film layer, preferably at least one nonwoven layer is hydrophobic. It may still be desirable to make both nonwoven layers hydrophobic to ensure that the bag is liquid impervious. Typically, the nonwoven layer may be treated with a surface active material, such as a fluorchemical or other hydrophobic finishings, to provide the requisite hydrophobicity. The nonwoven layer, however, may equally be treated with coatings of liquid impervious materials such as hot-melt adhesives or coatings of silicone or other hydrophobic compounds such as rubbers and vegetable and mineral waxes or it may be physically treated using nanoparticulates or plasma coating techniques, for example. The nonwoven layer can also be treated with agents to improve the tactile perceivable softness. The agents include but are not limited to vegetable, animal or synthetic oils, silicone oils and the like. The presence of these agents is known to impart a silky or flannel-like feel to the nonwoven layer without rendering it greasy or oily to the tactile sense of the wearer. Additionally, surfactant material, including anionic, non-anionic, cationic and non-cationic surfactants, may be added to further enhance softness and surface smoothness.

Suitable film materials for the bag 130 may comprise a thermoplastic material. The thermoplastic material can be selected from among all types of polyolefins especially polyethylene, polypropylene, amorphous polyolefins, and the like; material containing meltable components comprising fibers or polymeric binders including natural fibers such as cellulose, wood pulp, cotton, jute, hemp; synthetic fibers such as fiberglass, rayon, polyester, polyolefin, acrylic, polyamid, aramid, polytetrafluroethylene metal, polyimide; binders such as bicomponent high melt/low melt polymer, copolymer polyester, polyvinyl chloride, polyvinyl acetate/chloride copolymer, copolymer polyamide, materials comprising blends wherein some of the constituent materials are not meltable; air and vapour permeable materials including microporous films such as those supplied by EXXON Chemical Co., III, US under the designation EXXAIRE or those supplied by Mitsui Chemical Co., Japan under the designation ESPOIR NO; and monolithic breathable materials such as Hytrel™ available from DuPont and Pebax™ available from ELF Atochem, France. In a preferred embodiment, a film which is comprised in any layer is preferably permeable to gases such as air and to vapour such as water vapour in order to avoid the problem of entrapment and condensation of moisture vapour given off by the body of the wearer and thus, the hot, clammy and uncomfortable conditions after a short period of use.

The bag 130 may further contain an absorbent material therein. The absorbent material may be positioned inside the bag 130 in any suitable manner. For example, the absorbent material may be loosely arranged within the bag 130 or may be secured to the inner side of the bag 130. Any known techniques for securing absorbent material to nonwoven and film substrates may be used to secure the absorbent material to the inner side of the bag 130. The absorbent material may also be arranged to have any desired shape or configuration (e.g., rectangular, oval, circular, etc.). The absorbent material may comprise any material which is capable of absorbing and retaining discharged body fluids. The absorbent material may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers, synthetic fibers such as crimped polyester fibers; peat moss; tissue, including tissue wraps and tissue laminates; absorbent foams; absorbent sponges; superabsorbent polymers; superabsorbent hydrogel-forming polymeric material; absorbent gelling materials; or any other known absorbent material or combinations of materials or mixtures of these. The configuration and construction of the absorbent component comprising the absorbent material may also be varied, e.g., the absorbent component may have varying caliper zones (e.g., profiled so as to be thicker in the center), hydrophilic gradients, superabsorbent gradients, or may comprise one or more layers or structures.

The assistant tab 160 may be preferably disposed on the opposing surface 120 of the bag 130 as shown in FIGS. 2 and 4. The assistant tab 160 is provided to expand the bag 130 into a three-dimensional shape easily by pulling the assistant tab 160 after the device 100 is attached to the wearer.

Figure 3:
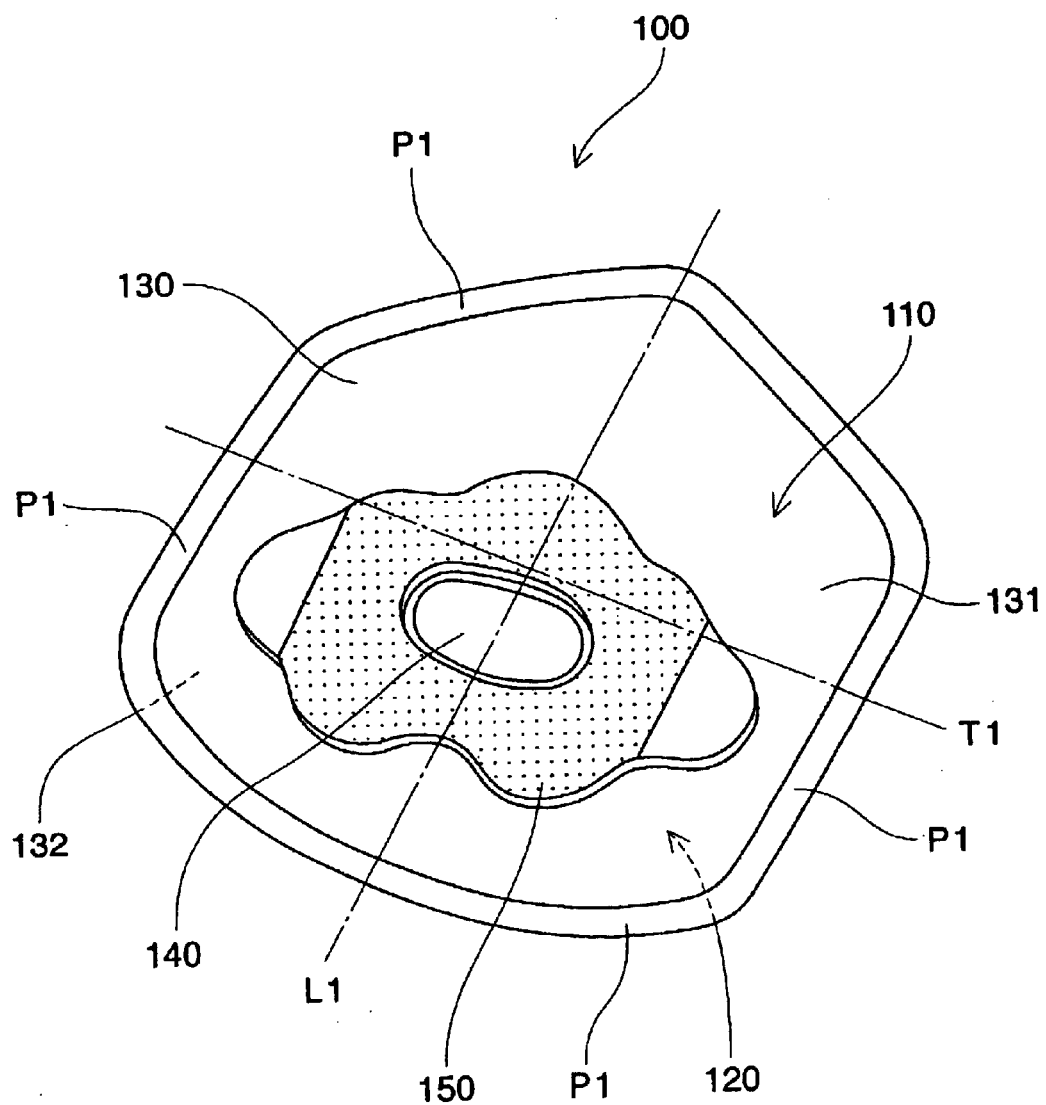
FIG. 3 is a perspective view showing the wearer-facing surface of the excreta management device of FIG. 1.

The opening 140 is formed on the wearer-facing surface 110 of the device 100 as shown in FIGS. 1 and 3 in order to receive excreta such as urine and/or fecal materials from an excretory orifice of the wearer prior to storage within the bag 130. The opening 140 is surrounded by the adhesive flange 150; and may be provided in any shape or size, such as circular, oblong, heart shaped and may be symmetrical or asymmetrical, preferably the opening has an oblong configuration either in the longitudinal direction or in the transversal direction.

The adhesive flange 150 is provided at the periphery of the opening 140 for adhesive attachment of the excreta management device 100 to the skin around the excretory orifice of a wearer as shown in FIGS. 1 and 3. The adhesive flange 150 is attached to the wearer-facing surface 110 of the excreta management device 100 by means known to the person skilled in the art, such as adhesives, heat bond, or the like. The adhesive flange 150 may be provided in any shape and preferably has a symmetrical slightly oblong shape in the longitudinal direction or in the transverse direction. Such suitable shapes include, but are not limited to: triangle shape; circle or oval shape; semicircle shape; sector shape; square, rectangular or diamond shape; a polygonal shape such as pentagon, hexagon, or the like; or any combination of the above. The adhesive flange 150 typically comprises an adhesive layer and a substrate to support the adhesive layer.

Figure 5:
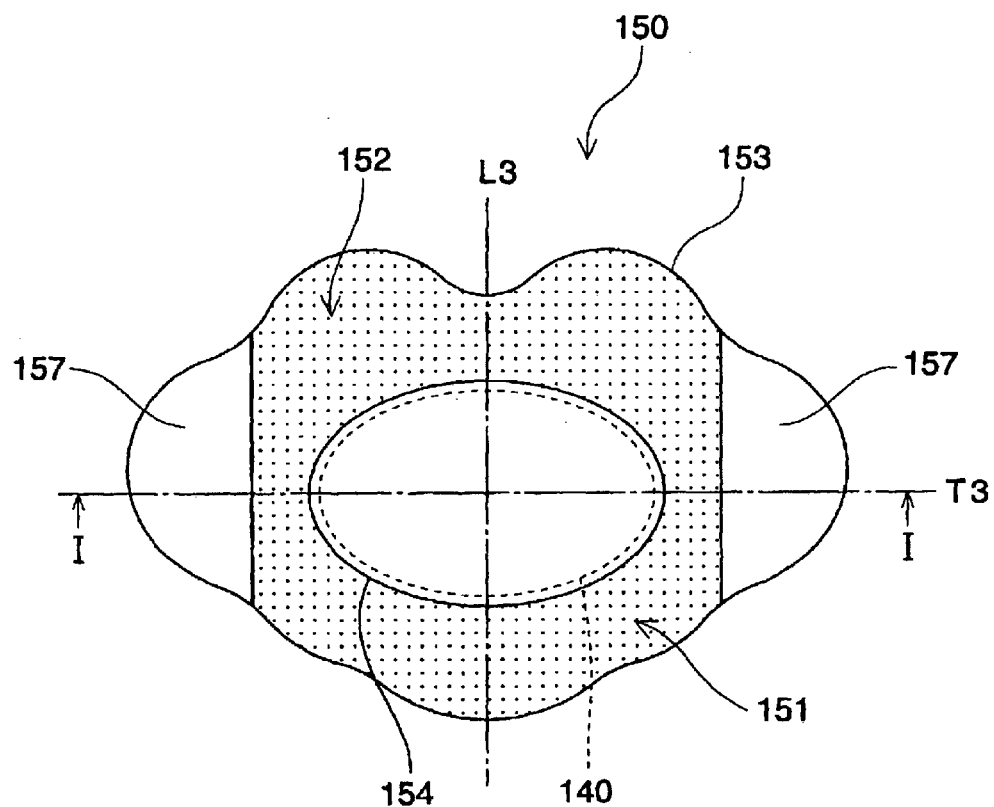
FIG. 5 is a top plan view of one embodiment of an adhesive flange constituting the excreta management device of the present invention.
Figure 6:
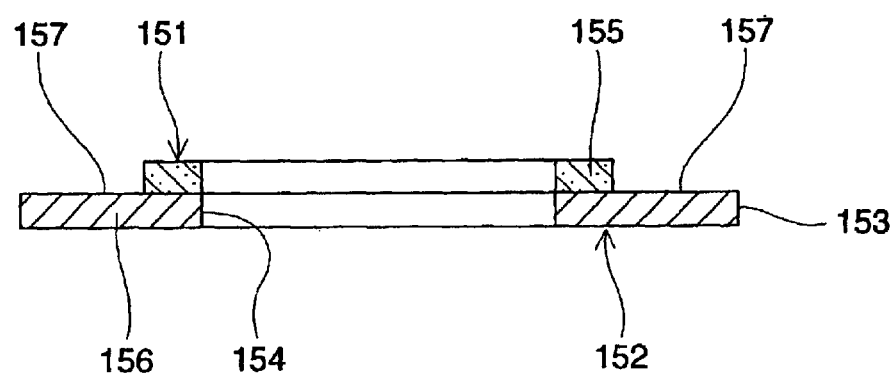
FIG. 6 is a cross-sectional view taken along line I—I of FIG. 5.

FIGS. 5 and 6 show a preferred embodiment of the adhesive flange 150 which is used for the excreta management device 100. The adhesive flange 150 shown in FIG. 5 has a longitudinal centerline L3 and a transverse centerline T3 which is perpendicular to the longitudinal centerline L3. The term "longitudinal", when used for the adhesive flange 150, refers to a line, axis or direction in the plane of the adhesive flange 150 that is substantially parallel to the longitudinal direction L1 of the excreta management device 100 when the adhesive flange 150 is equipped with the excreta management device 100. The terms "transverse" or "lateral", when used for the adhesive flange 150, refer to a line, axis or direction in the plane of the adhesive flange 150 that is generally perpendicular to the longitudinal direction. The adhesive flange 150 has two surfaces; one is a skin facing surface 151 and the other is a bag facing surface 152. The skin facing surface 151 is the surface of the adhesive flange 150 which is generally oriented toward the wearer's skin when the adhesive flange 150 is attached to the skin of a wearer. The skin facing surface 151 typically at least partially comes in contact with the wearer's skin during attachment of the adhesive flange 150 to the wearer's skin. The bag facing surface 152 is the surface of the adhesive flange 150 which is generally oriented away from the wearer's skin when the adhesive flange 150 is attached to the skin of a wearer, and which is generally oriented toward the flexible bag 130 when the adhesive flange 150 is joined to the bag 130. The term "joined" or "joining", as used herein, encompasses configurations in which an element is directly secured to another element by affixing the element directly to the other element; configurations in which the element indirectly secured to the other element by affixing the element to intermediate member(s) which in turn are affixed to the other element; and configurations in which one element is integral with another element, i.e. one element is essentially part of the other element. The adhesive flange 150, preferably, is joined to the flexible bag 130 constituting the excreta management device 100 such that the longitudinal centerline L3 of the adhesive flange 150 substantially corresponds to the longitudinal centerline L1 of the device 100. The adhesive flange 150 has an outer periphery 153 and an inner periphery 154. The inner periphery 154 of the adhesive flange 150 defines a generally circular aperture that is substantially aligned with the opening 140 of the bag 130 when the adhesive flange 150 is joined to the bag 130. The adhesive flange 150 comprises an adhesive layer 155 and a substrate 156 to support the adhesive layer 155. In a preferred embodiment, the substrate 156 is joined to the flexible bag 130 as another element. Alternatively, the substrate 156 may be integral with the flexible bag 130, i.e. the substrate 156 may be essentially part of the flexible bag 130. In addition, the substrate 156 may be omitted if the adhesive layer 155 is directly applied and supported on the surface of the bag 130. The adhesive flange 150 may be provided in any size depending on the wearer group for which the excreta management device 100 is intended.

The substrate 156 of the adhesive flange 150 should be made of soft, flexible and malleable material to allow easy placement of the adhesive flange 150 to the skin of a wearer. In addition, the substrate 156 of the adhesive flange 150 may be made of a hydrophobic material and/or a breathable material. Suitable materials for the substrate 156 of the adhesive flange 150 include but are not limited to nonwoven materials, and foams, such as open celled thermoplastic foams. An open-cell foam having a thickness within the general range of about 0.5 to 10 millimeters (preferably about 2 millimeters) has been found particularly effective. Other foam materials or other suitable plastics sheet materials having the described properties of such foams (i.e., softness, pliability, stretchability, contractability, breathability, and hydrophobicity) might be used.

The substrate 156 may comprise one or multiple layers, preferably two or three layers. The uppermost layer of the substrate 156, which will typically at least partially support the adhesive layer 155 thereon, is called the upper layer. The lowermost layer of the substrate 156, which will be typically at least partially joined to the bag 130, is called the lower layer. The layer of the substrate 156 may be provided from any material such that the substrate 156 is liquid impervious. The layer may in particular comprise any material such as a nonwoven or a polymeric film. In a preferred embodiment, the layer may be formed from a laminate comprising a nonwoven layer and a polymeric film. The upper layer of the substrate 156 is preferably provided with a nonwoven layer. The nonwoven upper layer presents a compliant surface to the skin of a wearer and sufficiently functions as a substrate to support the adhesive layer 155. In one preferred embodiment, the substrate 156 comprises two layers, which comprises a nonwoven layer as the upper layer and a film as the lower layer. The lower film makes the substrate 156 liquid impervious. Alternatively, the substrate 156 may comprise three layers; one film layer and two nonwoven layers, or two film layers and one nonwoven layer.

The adhesive layer 155 of the adhesive flange 150 comprises a body-compatible adhesive. The adhesive layer 155 is used in order to fix the adhesive flange 150 with the skin of a wearer while the device 100 is worn. Preferably, the adhesive layer 155 is covered with a release means to protect the adhesive layer 155 from contamination before use, such as siliconized paper or film. The adhesive layer 155 may cover the entire substrate 156, or alternatively, may partially cover the substrate 156 such that adhesive flange 150 has at least one, preferably a plurality of non-adhesive portions as removal tabs 157 to remove the excreta management device 100 from the skin of a wearer easily. The removal tabs 157 may be adhesive free or may contain inactivated or covered adhesives. The removal tabs 157 help users remove the device 100 from the skin of a wearer. In addition, the removal tabs 157 help users grip the device 100 for the attachment of the device 100 to the wearer's skin.

Any medically approved water resistant pressure sensitive adhesive may be used for the adhesive layer 155 constituting the adhesive flange 150 to attach the device 100 to the skin of a wearer, such as hydrocolloid adhesives and hydrogel adhesives. Particularly effective adhesives in providing the desired adhesive properties to secure the adhesive flange 150 to the skin of a wearer around the sensitive excretory orifice area, while allowing for relatively painless application and removal, are hydrophillic hydrogels formed from crosslinking polymers with a plasticizer to form a three-dimensional matrix. The adhesive to form the adhesive layer 155 can be applied to the substrate 156 of the adhesive flange 150 (or on the surface of the flexible bag 130 directly) by any means known in the art such as slot coating, spiral, or bead application or printing in order to form the adhesive layer 155.

The orifice 170 is provided on the flexible bag 130 for insertion of instruments or solid medicines such as wipes, an enema syringe, a suppository, and the like as shown in FIGS. 2, 4, 7 and 8. The orifice 170 allows easy insertion of such instruments or solid medicines into the bag 130. Therefore, a caregiver can easily give a wearer a treatment, such as an enema, insertion of a suppository, wiping the wearer's anus, through the orifice 170 and the opening 140 without removing the excreta management device 100. In a preferred embodiment, the orifice 170 is provided on the opposing surface 120 of the device 100. Alternatively, the orifice 170 may be provided on the wearer-facing surface 110 of the device 100. The orifice 170 may be provided on the opposing surface 120 so as to be positioned on the longitudinal centerline L1, more concretely, at the intersection of the longitudinal centerline L1 and the transverse centerline T1. The orifice 170 may be provided on the opposing surface 120 of the device 100 such that the orifice 170 is substantially aligned with the opening 140 when the bag 130 is not expanded. Such a position of the orifice 170 aligned with the opening 140 allows caregivers to easily treat the wearer's skin/excretory orifice through the orifice 170 and the opening 140 because caregiver can easily make the instruments, such as an enema syringe, a suppository or a wipe reach to the wearer's skin/excretory.

Figure 10:
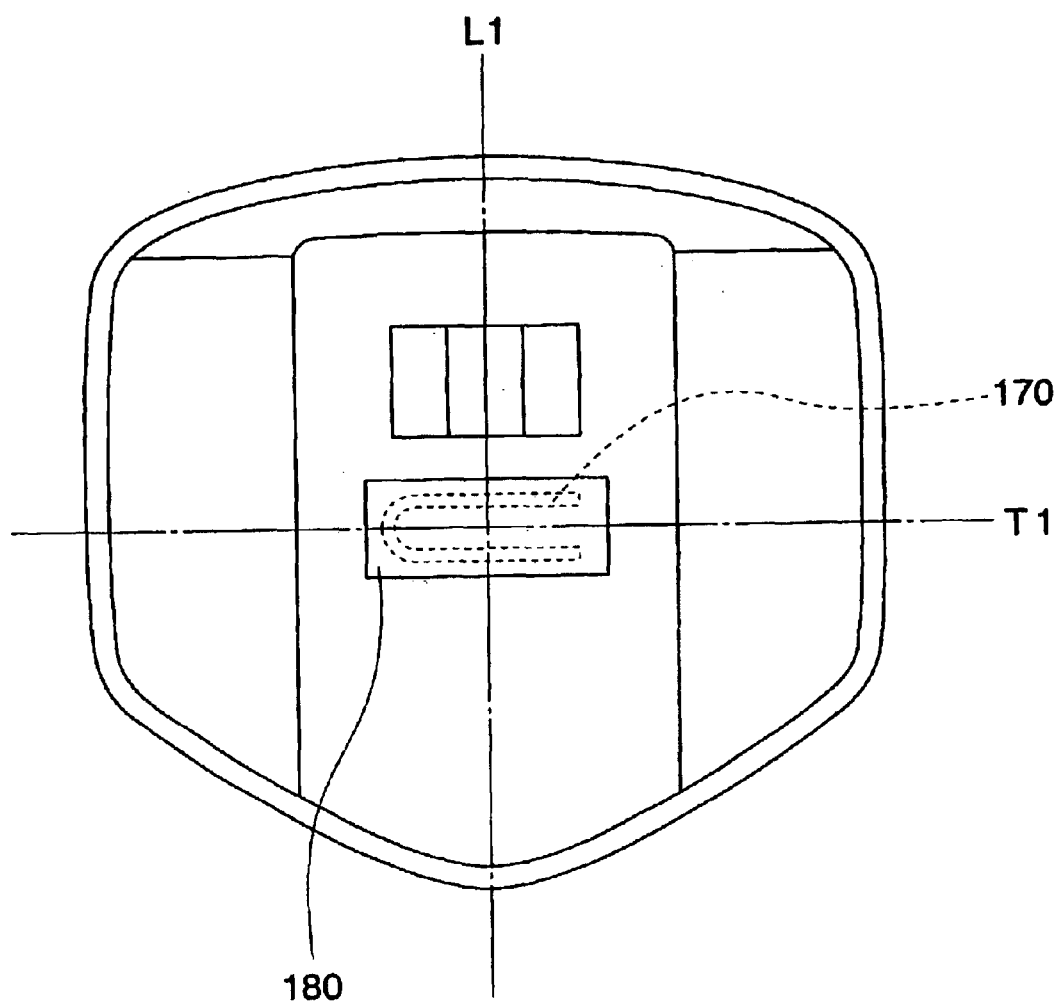
FIG. 10 is a bottom plan view of another embodiment of an excreta management device of the present invention.

The orifice 170 may be provided in any shape and preferably may have an oblong shape in the longitudinally direction or the transverse direction. Such suitable shapes include, but are not limited to: circle or oval shape; semicircle shape; sector shape; triangle shape; square, rectangular or diamond shape; a polygonal shape such as pentagon, hexagon, or the like; or any combination of the above. In a preferred embodiment, the orifice 170 may be a slit extending along one direction in the plane of the bag 130. In the embodiment shown in FIGS. 2, 4, 7 and 8, the orifice 170 is a slit extending along the transverse direction. Alternatively, such a slit may extend along the longitudinal direction or the diagonal direction. In another preferred embodiment, the orifice 170 may be a slit having an alphabet "U" configuration as shown in FIG. 10.

The orifice 170 may have any major dimension in any direction depending on the use for which the orifice 170 is intended. The term "major dimension", when used for the orifice 170, refers to the greatest dimension of the orifice 170. Such a dimension include, but are not limited to length, width, or a diameter. The orifice 170 may have a major dimension (e.g., the length "D" shown in FIG. 2) of between about 10 mm and about 200 mm, preferably between about 30 mm and about 100 mm, more preferably between about 50 mm and about 80 mm, if the excreta management device 100 is designed for adult wearers. In addition, the orifice 170 may have a major dimension (e.g., the length "D" shown in FIG. 2) of between about 10 mm and about 150 mm, preferably between about 20 mm and about 100 mm, more preferably between about 30 mm and about 50 mm, if the excreta management device 100 is designed for infant wearers.

Construction of the orifice 170 according to the particular dimension parameters given above results in a product with increased effectiveness. For example, if the orifice 170 is smaller than the particular dimension given above, it is difficult to insert the instruments, such as an enema syringe, a suppository or a wipe, into the bag 130 through the orifice 170. If the caregiver tries to forcibly insert the instrument into the bag 130 through the orifice 170 having such an undesirably small dimension, it could result in tearing the bag 130. In contrast, if the orifice 170 is bigger than the particular dimension given above, leakage of excreta contained into the bag 130 from the orifice 170 may occur during the use of the device 100 since it is difficult to completely seal the orifice 170 having such an undesirably big dimension while the device 100 is worn. In a preferred embodiment, the orifice 170 may have a major dimension D less than the interval C between the folds 134, 134 as shown in FIG. 2 if the orifice 170 is provided on the opposing surface 120 of the device 100 so as to be positioned between the folds 134, 134.

Figure 7:
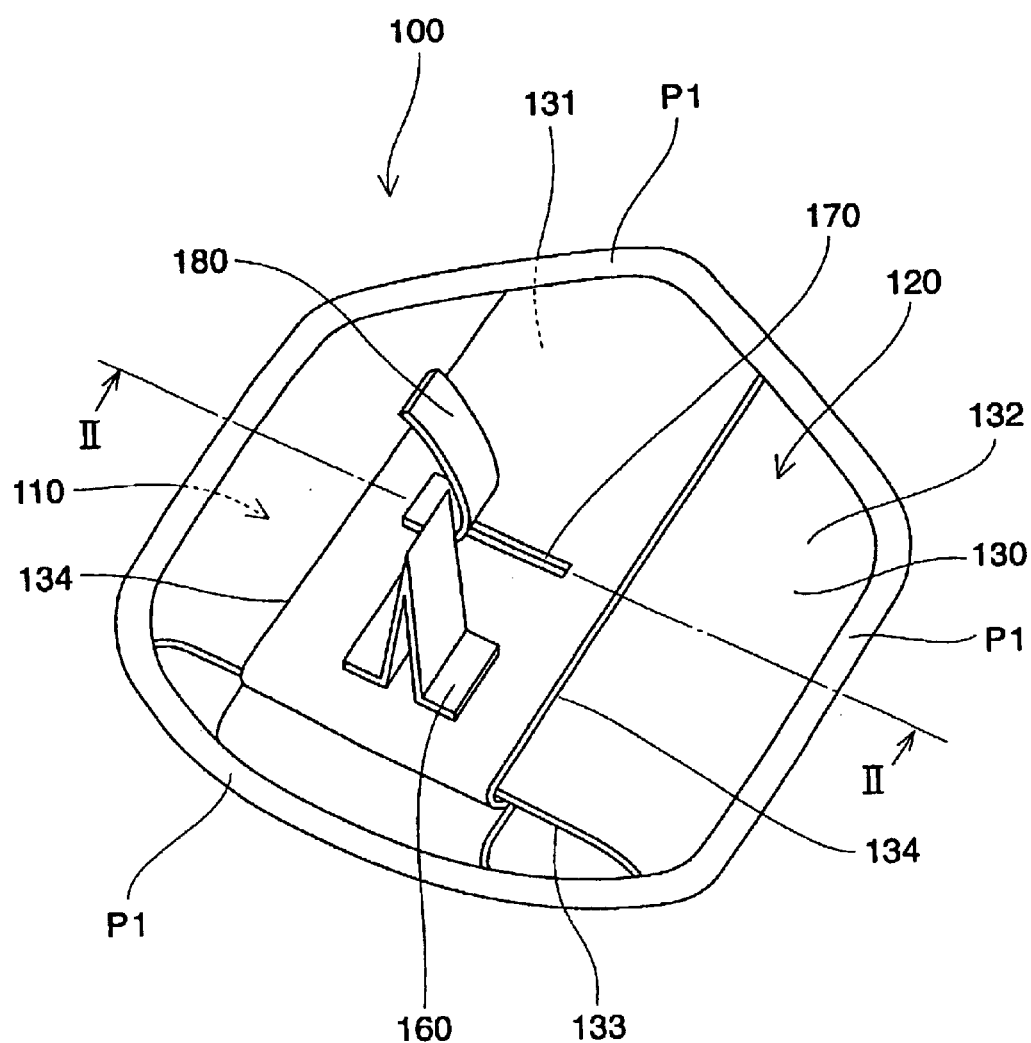
FIG. 7 is a perspective view showing the opposing surface of the excreta management device of FIG. 1 when the orifice cover is removed to expose the orifice.
Figure 8:
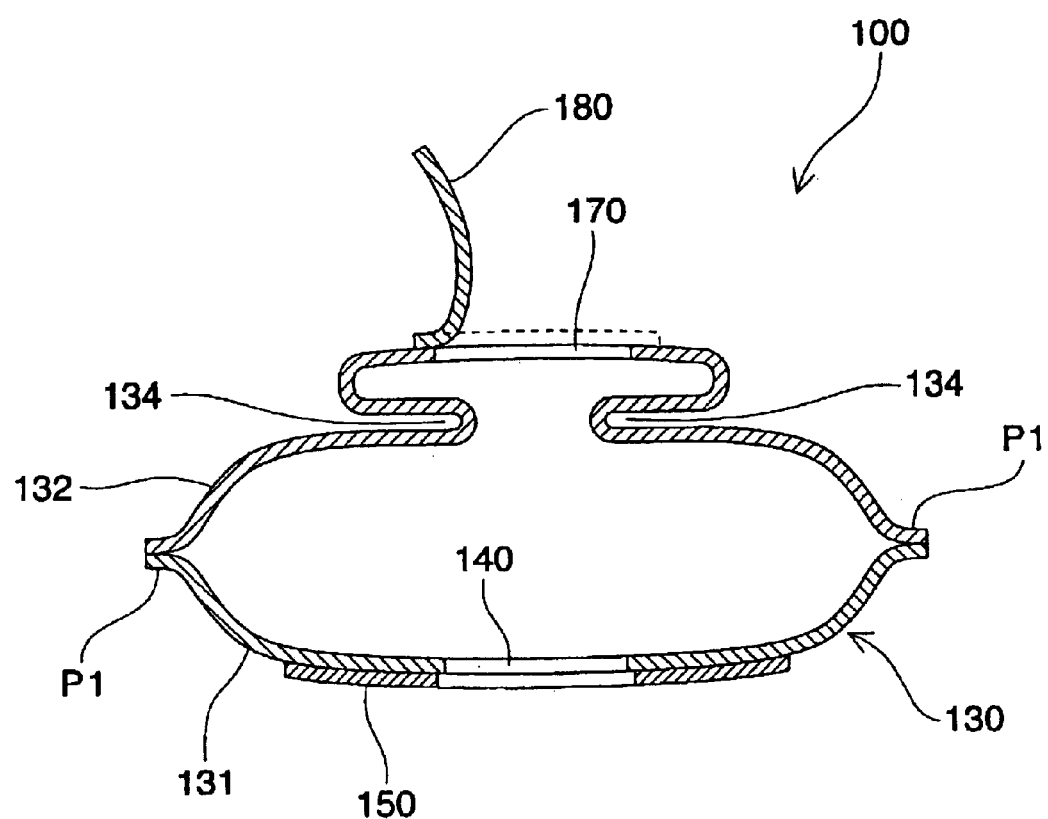
FIG. 8 is a cross-sectional view taken along line II—II of FIG. 7.

Seal means such as orifice cover 180 is provided over the orifice 170 for resealably sealing the orifice 170. The orifice cover 180 prevents discharged excreta from leaking through the orifice 170. Since the orifice cover 180 resealably closes the orifice 170, caregivers can give the wearer's excretory orifice a treatment, such as an enema, insertion of a suppository, and/or wiping the wearer's anus, through the orifice 170 repeatedly during the use of the device. The orifice cover 180 may be attached to the bag 130 such that a part of the orifice cover 180, preferably one end of the orifice cover 180 as shown in FIGS. 7 and 8, is fixed to the bag 130. Alternatively, the orifice cover 180 may be attached to the bag 130 such that the entirety of the orifice cover 180 can be removed from the bag 130. The orifice cover 180 may be provided in any shape and any size as long as the orifice cover 180 seals the orifice 170 so as to prevent leakage of discharged excreta from the orifice 170. Such suitable shapes include, but are not limited to: circle or oval shape; semicircle shape; sector shape; triangle shape; square, rectangular or diamond shape; a polygonal shape such as pentagon, hexagon, or the like; or any combination of the above. The orifice cover 180 should be made of soft, flexible and malleable material to allow conformance of the orifice cover 180 with movement of the wearer and deformation of the flexible bag 130 while the device 100 is worn. In addition, the orifice cover 180 may be made of a hydrophobic material and/or a breathable material. Suitable materials for the orifice cover 180 include but are not limited to film materials. Alternatively, such materials for the orifice cover 180 may be nonwoven materials. The above-mentioned suitable nonwoven and film materials for the flexible bag 130 can be utilized as the material for the orifice cover 180. The orifice cover 180 may have a layer of adhesive applied onto the surface thereof for resealable adhesive attachment of the orifice cover 180 to the bag 130. Alternatively, the adhesive may be applied onto the surface of the bag 130 where the orifice cover 180 is resealably attached to close the orifice 170. Any suitable adhesive may be used as long as it provides the desired attachment strength required for having resealable function. Such adhesive for resealable adhesive attachment may be, e.g., a pressure sensitive adhesive, applied by any known coating processes (e.g., a slot coating process, a solvent coating process, and the like).

The adhesive is, preferably, an elastomeric pressure-sensitive adhesive. It is particularly preferred that such an adhesive comprises a tackified rubber elastomer. In order to facilitate the release of the orifice cover 180 from the bag 130, the surface of either the orifice cover 180 or the bag 130 may be applied with a release agent, preferably a silicone release coating. The orifice cover 180 may be partially attached to the bag 130 by adhesive as long as the orifice cover 180 closes the orifice 170 so as to prevent discharged excreta from leaking. In such a case, the non adhesively attached part of the orifice cover 180 functions as a tab to expand the bag 130 into a three-dimensional shape by pulling the non adhesively attached part of the orifice cover 180. This enables the assistant tab 160 to be omitted.

The orifice cover 180 is attached to the bag 130 such that the orifice cover 180 and the surface of the bag 130 should interact to resist a peel force occurring while the device 100 is worn. The term "peel force", as used herein, refers to forces to separate one component of the device 100 from another component of the device 100 when such components are attached to each other. In addition, the orifice cover 180 is attached to the bag 130 such that the orifice cover 180 resealably closes the orifice 170 while the attachment of the orifice cover 180 to the bag 130 resists the peel force described above. Therefore, the peel force of the orifice cover 180 to the bag 130 should not be too great since the orifice cover 180 and/or the bag 130 may tear when the orifice cover 180 is removed to expose the orifice 170. Thus, the peel force of the orifice cover 180 to the surface of the bag 130 should be preferably between about 0.3 N/cm and about 4.0 N/cm, more preferably between about 0.8 N/cm and about 2.1 N/cm, even more preferably about 0.9 N/cm and about 1.6 N/cm.

A peel force value is measured according to the method described hereinafter. This method describes the procedure for measuring the peel force, in N/cm, of the combined the material of the orifice cover 180 and the material of the bag 130. The suitable instrument used for the measurement of the peel force for the orifice cover 180 and the bag 130 is INSTRON 5564 which may be equipped with either digital readout or strip chart data display for load and elongation. The following procedure is conducted under standard laboratory conditions at 23° C. (73° F.) and 50% relative humidity for a minimum of 2.0 hours.

(1) Cut a material of the orifice cover 180 into a strip having 80 mm by 25 mm size to make Sample A, and a material of the bag 130 into a strip having 100 mm by 25 mm size to make Sample B. The one surface of Sample A is applied a pressure sensitive adhesive in an area of 55 mm by 25 mm from the one edge thereof for the adhesively attachment of Sample A to Sample B. The remaining area of Sample A is not applied a pressure sensitive adhesive. Alternatively, Sample A may be also made by cutting a material of the orifice cover 180 into a strip having 60 mm by 25 mm size, and then applying a pressure sensitive adhesive in a whole area of one surface of the strip, and then attaching an additional tab having 25 mm by 25 mm size to the one edge of the strip.

(2) Attach Sample A on Sample B to make a sample strip such that the one edge of Sample A which is applied a pressure sensitive adhesive and the one edge of Sample B correspond with each other. Because the other edge of Sample A is not applied a pressure sensitive adhesive, the other edge of Sample A and that of Sample B are not adhesively attached to each other, and form non-attached tabs for allowing them to be gripped by the clamps of the instrument. At least 10 sample strips should be prepared for the measurement.

(3) Roll a rubber coated steel roller of diameter of 135 mm, a width of 45 mm and a weight of 5 kg, forth and back on the sample strip in the length direction of the sample strip once (a total of twice passes).

(4) Put the sample strip in the instrument. The way to set the sample strip is to insert the non-attached tab of Sample A into the top clamp of the instrument first, and then to insert the non-attached tab of Sample B into the bottom clamp with enough tension to eliminate any slack of the sample strip.

(5) Peel Sample A of the sample strip from Sample B of the sample strip at a peeling speed of 300 mm/minute until completely separating them from each other.

(6) Read the peel force values in a peeling range between 10 mm and 100 mm (i.e., a change of the distance between the top clamp and the bottom clamp).

(7) Calculate an average value of the peel force values which are read in the procedure (6).

(8) Repeat the above procedures (1) to (7) for the other sample strips.

(9) Calculate the Peel Force as follows:

Peel Force=Sum of the average peel force values of the procedure (7) for samples tested
(N/cm) Number of test strips tested Attachment of the orifice cover 180 to the surface of the bag 130 according to the particular peel force parameters given above results in a product with increased effectiveness. For example, if the peel force of the orifice cover 180 to the bag 130 is less than the particular peel force given above, the orifice cover 180 will easily come off from the bag 130 while the device 100 is worn. This may result in leakage of excreta contained into the bag 130 through the orifice 170 during the use of the device 100. In contrast, if the peel force of the orifice cover 180 to the bag 130 is greater than the particular peel force given above, it is difficult for caregivers to remove the orifice cover 180 from the bag 130 in order to expose the orifice 170. In such a case, if the caregiver forcibly tries to remove the orifice cover 180 from the bag 130, the orifice cover 180 and/or the bag 130 may even tear.

Figure 9:
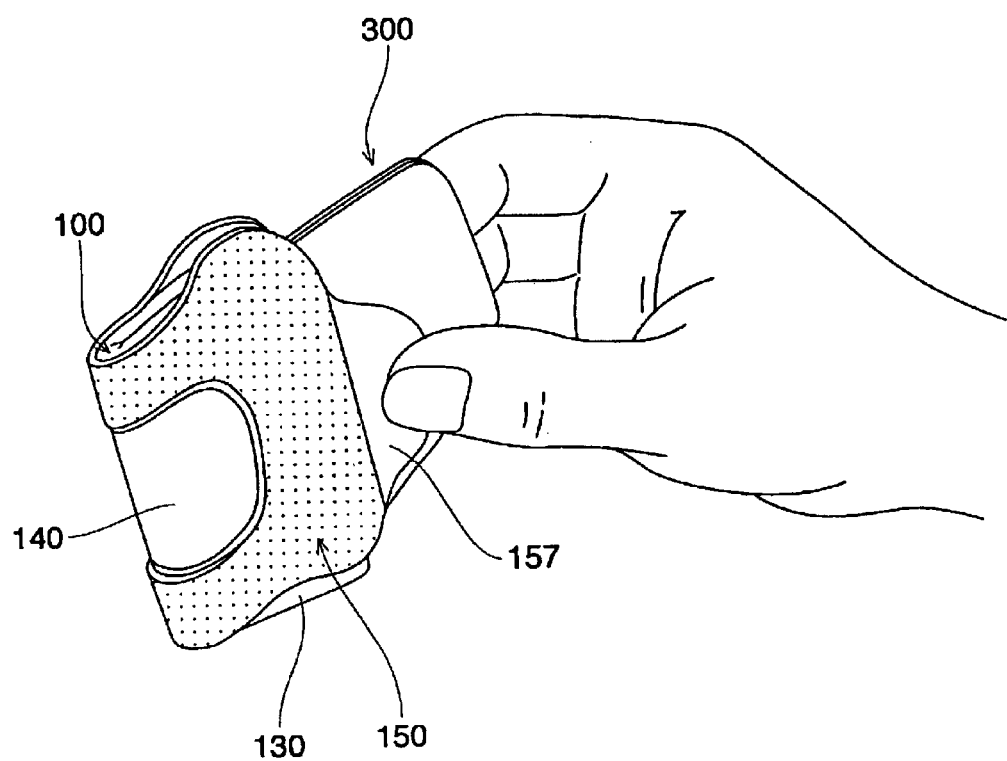
FIG. 9 is a perspective view of the excreta management device of FIG. 1 when the device is held by the user.

As shown in FIG. 9, the excreta management device 100 may be equipped with an applicator 300 before the device 100 is worn. For secure adhesive attachment of the device 100, pressure needs to be exerted onto the device 100 and the skin of a wearer to ensure adhesion. The applicator 300 allows the user to easily apply sufficient pressure to the device 100 toward the skin of a wearer for adhesive attachment of the device 100. In addition, the applicator 300 allows the user to control such pressure such that pressure is exerted onto the correct/desired area of the skin of a wearer. In a preferred embodiment, the excreta management device 100 is provided in a particular form prior to the use of the device 100. In that configuration, the adhesive flange 150 is folded into a pair of two pieces for the easy placement of the flange 150, e.g., between the buttocks of the wearer. In addition, the bag 130 may be preferably folded such that the bag 130 is substantially completely disposed between the two pieces of the folded adhesive flange 150. More preferably, the excreta management device 100 in combination with the applicator 300 is provided in a particular form prior to use as shown in FIG. 9. Such a form of the device 100 and the applicator 300 provides numerous advantages. For example, folding of the device 100 and the applicator 300 facilitates a compact packaging form of the device 100 and the applicator 300. Thus, it is possible to reduce the costs for transport and packaging material. In addition, the folded device 100 in combination with the applicator 300 enables the user to easily handle the device 100 equipped with the applicator 300 since the device 100 may otherwise completely cover the applicator 300. The unfolded device 100 may also cover parts of the skin of the wearer such that the user placing the device 100 cannot sufficiently visually control placement of the device 100.

The use of the excreta management device 100 according to the present invention preferably comprises the following steps:

(a) Taking out the device 100 and the applicator 300 from the package while gripping both the tabs 157 of the adhesive flange 150 and the applicator 300 by using one hand as shown in FIG. 9;

(b) Supporting the body of a wearer, such as wearer's legs by using the other hand for placement of the device 100;

(c) Placing the device 100 in the area around the excretory orifice of the wearer such as the perianal area by using the applicator 300;

(d) Letting the adhesive layer 155 of the adhesive flange 150 of the device 100 attach to the area around the excretory orifice of the wearer by using the applicator 300;

(e) Exerting force to press the device 100 toward the area around the excretory orifice of the wearer through the applicator 300;

(f) Pressing the entire adhesive layer 155 of the adhesive flange 150 toward the area around the excretory orifice of the wearer through the applicator 300;

(g) Separating the applicator 300 from the device 100;

(h) Unfolding the bag 130 of the device 100;

(i) Pulling the assistant tab 160 disposed on the bag 130 to expand the bag 100 into a three-dimensional shape;

(j) Opening the orifice 170 by removing the orifice cover 180;

(k) Inserting instruments, such as wipes, an enema syringe, a suppository, or the like, into the bag 130 through the exposed orifice 170;

(l) Giving the wearer's excretory orifice (or the skin around the excretory orifice) a treatment, such as wiping the wearer's excretory orifice, an enema, or insertion of a suppository, through the opening 140;

(m) Closing the orifice 170 by the orifice cover 180 again after the treatment.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable excreta management device having a longitudinal centerline, a transverse centerline, a wearer-facing surface and an opposing surface, the disposable excreta management device comprising a flexible bag to contain excreta and an adhesive flange to attach the device to the body of a wearer, the flexible bag having an opening positioned on the wearer-facing surface, wherein the excreta management device has an orifice provided on the flexible bag and comprises a seal means to resealably close the orifice, and a peel force of the seal means to the surface of the flexible bag is between 0.3 N/cm and 4.0 N/cm wherein the orifice is positioned on the opposing surface and wherein the orifice is positioned at the intersection of the longitudinal centerline and the transverse centerline.

2. A disposable excreta management device of claim 1 wherein the orifice is aligned with the opening when the bag is not expanded.

3. A disposable excreta management device of claim 1 wherein the opposing surface of the device is translucent or transparent.

4. A disposable excreta management device of claim 1 wherein the orifice has a major dimension of between 10 mm and 200 mm.

5. A disposable excreta management device of claim 1 wherein the orifice is a slit.

6. A disposable excreta management device of claim 1 wherein the seal means comprises an orifice cover attached to the flexible bag.

* * * * *